United States Patent
Campagna et al.

[11] 3,934,590
[45] Jan. 27, 1976

[54] OCULAR POSITIONING DROPLET DISPENSING DEVICE

[76] Inventors: Gary J. Campagna, 236 Willow Ave.; Roland C. Janson, 114 Granada Drive, both of Corte Madera, Calif. 94925

[22] Filed: Nov. 21, 1974

[21] Appl. No.: 525,761

[52] U.S. Cl. ................................ 128/233; 128/249
[51] Int. Cl.² .......................................... A61M 7/00
[58] Field of Search ............ 128/233, 249; 222/105, 222/181, 184, 192, 420

[56] References Cited
UNITED STATES PATENTS

| | | | |
|---|---|---|---|
| 847,014 | 3/1907 | Lee | 222/181 |
| 2,560,377 | 7/1951 | Waterman | 222/181 X |
| 3,279,466 | 10/1966 | Mings | 128/233 |
| 3,405,843 | 10/1968 | Watson | 222/105 X |
| 3,439,674 | 4/1969 | Lelicoff | 128/233 |

FOREIGN PATENTS OR APPLICATIONS
1,263,954   12/1960   France ................................ 128/233

*Primary Examiner*—Robert B. Reeves
*Assistant Examiner*—Larry H. Martin
*Attorney, Agent, or Firm*—Warren, Chickering & Grunewald

[57] ABSTRACT

A tripod support having a wall and three legs connected to and diverging therefrom substantially symmetrical to an axis perpendicular to the wall. A distal end of one of the legs is formed for mounting on the bridge of the nose of the user. The other two legs are located for resting upon the user's brow and cheekbone in spanning relation to the eye. A standard size soft-sided squeeze bottle of ophthalmic liquid is mounted with its reduced droplet discharge end mounted through an opening in the support wall so as to align the bottle discharge with the user's eye.

3 Claims, 5 Drawing Figures

OCULAR POSITIONING DROPLET DISPENSING DEVICE

BACKGROUND OF THE INVENTION

1. Field of Invention

The invention relates to devices designed for the self-administration of ophthalmic solution in droplet form to the eye or eyes of the user; and more particularly to such devices having facial contacting parts for assisting the user in locating the droplet discharge opening in registration with an eye.

2. Description of Prior Art

Prescription and non-prescription eyedrops are widely used for the care and treatment of the eyes. Conventionally and almost universally such eyedrops are packaged in a standard size, soft-sided squeeze bottle having a nozzle with a discharge opening therein, and the bottle is held in inverted position over the eye to be treated and squeezed to discharge one or more drops of the ophthalmic solution into the eye. In many instances such drops must be self-administered by persons suffering from glaucoma, or otherwise having poor vision, or little vision at all; and frequently such self-administration is by preference or requirement done in the dark. Under such circumstances self-administration of eyedrops can be difficult, wasteful of precious material, and even dangerous due to frequent accidental physical contact of the bottle nozzle with the eye and resulting injury to the sclera.

Various structures have been proposed having a tactile part appropriately spaced from the droplet discharge opening and adapted for engagement with various facial areas such as the nose, cheekbone, and the like, for locating the discharge nozzle in alignment over the eye. Since the eyedrops may be used several times a day and over a long period of time, it is imperative that the face-contacting, locating, structure not engage facial portions closely adjacent to the eye in order to avoid possible transmission of infection to the eye. Generally the prior proposed structures with which we are familiar do not prevent tipping of the bottle nozzle into injurious contact with the eye or positively locate the nozzle in aligned position with the eye, while at the same time avoiding contacting the peripheral portion of the eye or a facial portion immediately adjacent thereto.

SUMMARY OF INVENTION

The present invention employs a tripod eye droplet bottle support, bridging the eye to be treated, and positively indexing on the bridge of the user's nose for simple, easy and very precise self-administration of liquid eyedrops, and in which at all times the eye is protected against impingement by the droplet discharge nozzle or any other part of the device, and all facial contacting parts of the device have minimal contact area well removed from the eye being treated.

Another object of the present invention is to provide an ocular positioning droplet dispensing device of the character described which will be handled and positioned by only one hand of the user leaving the other hand free to assist in holding open the eye being treated.

A further object of the present invention is to provide an ocular positioning droplet dispensing device of the character above which with minimal training or experience can be quickly and easily positioned over the eye to be treated, and with equal ease and facility flipped from one eye to the other.

Still another object of the present invention is to provide an ophthalmic droplet dispensing device of the character described in which the dispensing bottle is normally maintained in an inverted position, that is with its dispensing nozzle lowermost, thus automatically causing ophthalmic liquid in the bottle to become free of entrapped air bubbles and to cause the air to separate into the upper portion of the bottle with clear, unaerated liquid settling in the bottom of the bottle in discharging position over the nozzle. This feature is of particular importance where viscus ophthalmic liquid is used by a doctor in the course of examination and where an optically clear liquid must be deposited in the eye being examined. The presence of small air bubbles entrapped in the liquid may terminate the examination.

The invention possesses other objects and features of advantage, some of which of the foregoing will be set forth in the following description of the preferred form of the invention which is illustrated in the drawing accompanying and forming part of this specification. It is to be understood, however, that variations in the showing made by the said drawing and description may be adopted within the scope of the invention as set forth in the claims.

Referring to said drawing:

DETAILED DESCRIPTION OF INVENTION

Figure 1:
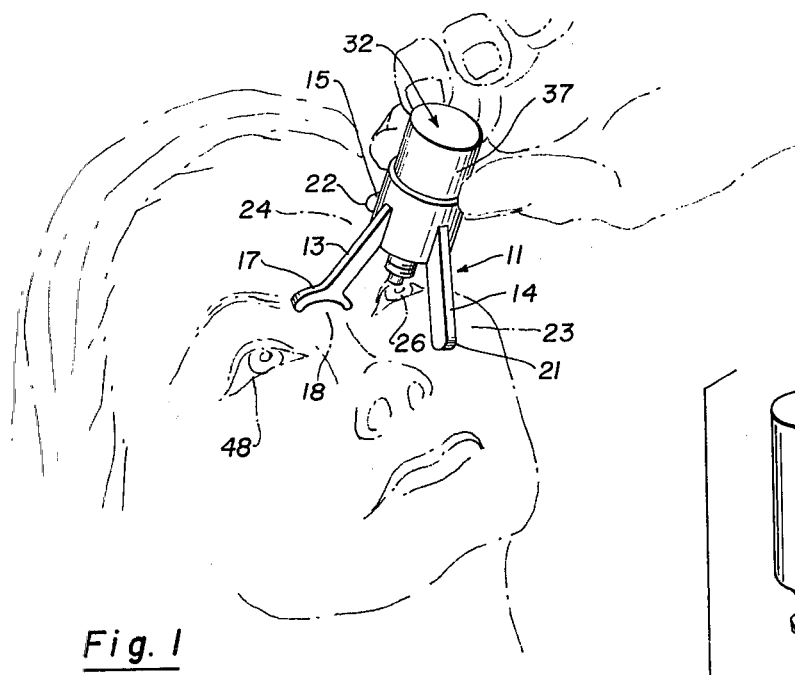
FIG. 1 is a perspective view of an ocular positioning droplet dispensing device constructed in accordance with the present invention and shown in operative position on the face of the user.

The ocular positioning droplet dispensing device of the present invention comprises briefly a tripod support 11 having a wall 12 and three legs 13, 14 and 15 connected to and diverging from wall 12 substantially symmetrical to an axis 16 perpendicular to wall 12; the distal end 17 of leg 13 being formed (notched) for mounting on the bridge 18 of the nose of the user; the other two legs 14 and 15 extending from wall 12 on opposite sides of leg 13 and having spaced apart distal ends 21 and 22 for resting upon the user's cheekbone 23 and brow 24, respectively, in spanning relation to the user's eye 26; wall 12 having an opening 27 therein medially of legs 13-15 and on axis 16 and dimensioned for receiving therethrough the nozzle discharge end 31 of a dispensing squeeze bottle 32 of ophthalmic liquid, wall 12 supporting bottle 32 in position aligning nozzle 31 on axis 16 and with the user's eye 26.

Preferably support 11 also includes an annular wall 36 disposed substantially concentric to axis 16 and dimensioned for slideably receiving and supporting the side wall 37 of a standard size squeeze bottle 32. Eyedrops, both prescription and non-prescription, are almost universally dispensed in a 15 cc softsided squeeze bottle of about one inch outside diameter. The interior surface of wall 36 may be provided, as here shown, with a plurality of circumferentially spaced, longitudinally extending ribs 38 for firmly gripping and in some instances partially deforming the bottle side wall 37 so as to adapt the present device to bottles having minor variations in their diameters. Preferably, annular wall 36 is of cylindrical shape having a normally lower end 39 joined integrally with the outside periphery of wall 12, which is here of disc shape extending perpendicularly across wall 36 and forming a cup-shaped receptacle for bottle 32.

Figure 3:
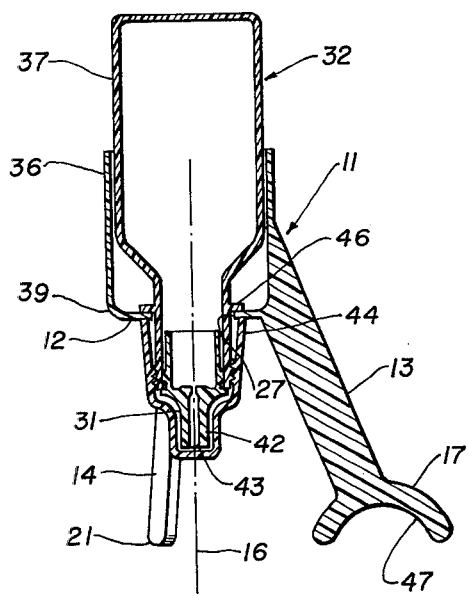
FIG. 3 is a longitudinal, cross-sectional view of the device and bottle.
Figure 4:
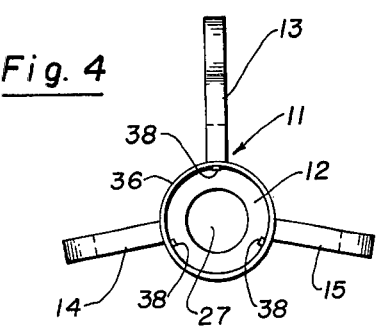
FIG. 4 is a plan view of the device.

The standard eyedropper bottle is formed with a reduced, substantially cylindrical neck 41 which is fitted with a discharge nozzle 42 having a droplet discharge opening 43. A cap 44 is threadably attached to neck 41 to provide a demountable closure for droplet discharge opening 43. Also, the standard droplet squeeze bottle 32 is formed with a flange on neck 41 adjacent its base. Cooperating with the above structure, opening 27 is dimensioned for receiving neck 41 therethrough, as seen in FIG. 3, permitting flange 46 to rest on and be supported by wall 12. When the bottle and device are so assembled, neck 41 will project through wall 12 to the underside thereof, as seen in FIG. 3, and when the device is not in use, cap 44 may be attached to neck 41 to enclose nozzle opening 43 and to hold the parts in assembled position. Preferably, cap 44 may be threaded onto neck 41 to a position engaging the base of the cap against the underside of wall 12 so as to firmly interlock the parts together.

To use the device, cap 44 is first removed so as to expose discharge nozzle 42. Bottle 32 will remain firmly gripped by wall 36 so that the assembly may be moved as a unit into position over the eye 26 to be treated, as illustrated in FIG. 1. The mounting of the device in its operative position, as illustrated in FIG. 1, is easily and readily effected by first positioning the lower end 17 of leg 13 onto the bridge of the user's nose and then swinging the assembly about end 17 and in a clockwise direction, as seen in FIG. 1, until the lower ends 21 and 22 of legs 14 and 15 rest on the user's cheekbone and brow. To facilitate the indexing of the device on the user's nose, lower end 17 is formed as an arched foot having a concave underside 47 which will fit over and mate with the convex shape of the nose bridge thus rotationally indexing the position of the device. The lateral spacing of end 17 from axis 16 will locate axis 16 in alignment with the user's eye. Since it is not essential that drops be applied directly to the center of the eye, an average spacing between axis 16 and foot 17 may be selected for insuring proper droplet administration for persons having a wide difference in interpupillary spacing. When the device has been positioned as illustrated and described, the operator may engage the soft side 37 of bottle 32 extending exteriorly from annular wall 36 and apply a squeezing pressure to the bottle side wall to eject one or more drops from nozzle opening 43 and into the eye being treated. Since the bottle is firmly held within the surrounding support wall 36, the assembly may be handled entirely be engagement with the exposed side wall of the bottle. To treat the user's other eye 48, it is only necessary to flip the device around by 180° again locating foot 17 on the bridge of the user's nose and supporting legs 14 and 15 in spanning relation to eye 48. In all of the above operations, the device may be handled and operated with one hand thereby leaving the user's other hand available for holding open the eye being treated, if so desired.

Of greatest importance in the foregoing operation is the fact that the device may be readily properly located in position for use by a person having poor or even no eyesight, or while using the device at night in a darkened room. In all such instances, it is only necessary for the user to locate foot 17 on the nose bridge and then lower the device until legs 14 and 15 contact the cheekbone and brow. Thus, it is impossible for the user to accidentally move the bottle nozzle 42 to impact the eye, a possibility which may occur with other devices with which we are familiar, with potential injury to the eye. Also, it will be noted that all parts of the device which have facial contact are well spaced from the eye being treated so as to eliminate the potential transmission of infection or contaminants to the eye being treated.

Figure 2:
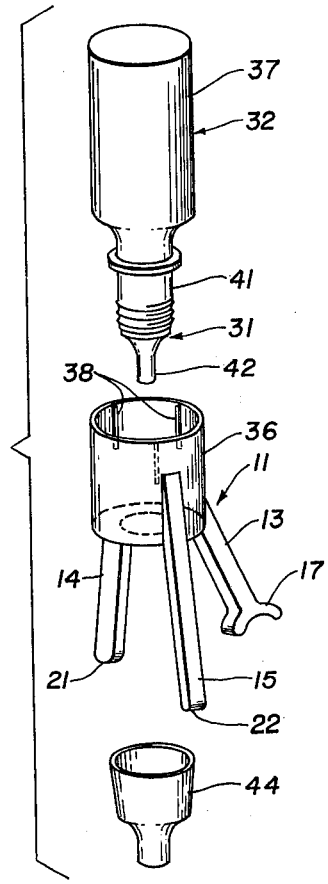
FIG. 2 is an exploded perspective view of the device and standard eye dropper bottle.
Figure 5:
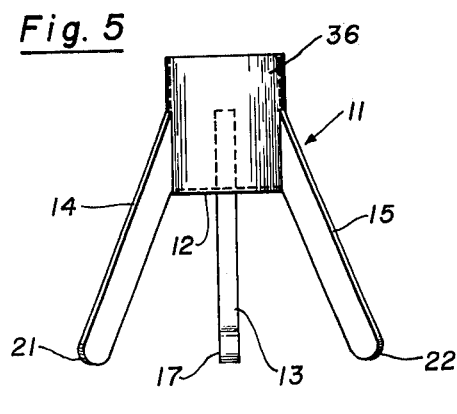
FIG. 5 is a front elevation of the device.

While the device is designed for self-administration of eyedrops by the user, it is also designed to provide important advantages to an ophthalmologist in making an examination of an eye of his patient. Such procedures may call for the use of a viscus liquid. Inversion of the eyedropper bottle, even when done slowly and with care, will likely cause entrapment of air in the liquid with resultant discharge of an aerated solution which may impair and even terminate the examination being conducted. This result may only be avoided by the doctor waiting a significant time after inversion of the bottle to permit the entrapped air to settle out of the solution. The present device provides an important advantage in avoiding the foregoing problems in normally maintaining the bottle in an inverted position so that the long periods between use automatically function to cause entrapped air to separate out of the liquid and to accumulate in the top of the bottle while clear, unaerated liquid settles into the lower portion of the bottle in discharging position over the nozzle. Consequently, when the device is picked up for use by the doctor, no inversion of the bottle is involved. With reference particularly to FIG. 5, it will be noted that the lower ends of the three legs 13, 14, 15 terminate in a common normally horizontal plane substantially parallel to the plane of opening 27 and wall 12. The device thus provides a stable tripod support on a table top or the like, holding bottle 32 in its inverted position, as seen in FIGS. 2 and 3 in the nonuse storage mode of the device.

What is claimed is:

1. An ocular-positioning device for a standard soft-sided squeeze bottle of ophthalmic liquid having a reduced externally threaded droplet discharge nozzle and an internally threaded closure cap threadable on said nozzle, comprising:

an open top socket having a bottom wall formed with a normally horizontally disposed medial opening therein dimensioned to receive said nozzle and having an upstanding circumferentially disposed support structure on said wall, said structure being formed to slidably receive and embrace and support in vertically inverted position the side wall of said bottle with said nozzle extending through said opening;

a leg secured to and depending from said socket and having a concavely notched lower end structured to seat upon and rotationally index with the bridge of the user's nose and to position said opening in vertically spaced alignment over the user's eye;

a pair of legs secured to and depending from said socket and having lower ends spaced on opposite sides of the axis of said opening and spaced from said first-named end and positioned to engage and rest upon the user's brow and cheek bone and to support said nozzle in spaced relation to the user's eye, the lower ends of said legs terminating in a common normally horizontal plane substantially parallel to the plane of said opening for supporting said device and said inverted bottle on a table top or the like in the storage mode of said device; and said cap being threadable onto said nozzle at the normally under side of said wall to demountably secure said bottle in inverted position in said socket in said storage mode of said device.

2. A device as defined in claim 1, said wall being substantially disc-shaped, and said structure comprising a plurality of circumferentially spaced vertically extending ribs.

3. A device as defined in claim 2, said bottle being formed with a flange adjacent said nozzle and said opening being sized to retain said flange on the normally upper side of said wall; and said cap bearing on the normally under side of said wall to clamp said wall between said cap and flange.

* * * * *